(12) United States Patent
Seitz et al.

(10) Patent No.: US 11,458,246 B2
(45) Date of Patent: Oct. 4, 2022

(54) METHODS AND SYSTEMS FOR DETECTING INFUSION PUMP CONDITIONS

(71) Applicant: Tandem Diabetes Care, Inc., San Diego, CA (US)

(72) Inventors: Alexander Seitz, Delmar, CA (US); Michael Michaud, San Diego, CA (US); Philip Sven Lamb, San Diego, CA (US); Justin Brown, San Diego, CA (US); Geoffrey A. Kruse, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 169 days.

(21) Appl. No.: 16/266,471

(22) Filed: Feb. 4, 2019

(65) Prior Publication Data
US 2019/0240398 A1 Aug. 8, 2019

Related U.S. Application Data

(60) Provisional application No. 62/632,294, filed on Feb. 19, 2018, provisional application No. 62/626,430, filed on Feb. 5, 2018.

(51) Int. Cl.
*A61M 5/142* (2006.01)
*A61M 5/168* (2006.01)
(Continued)

(52) U.S. Cl.
CPC ...... *A61M 5/14244* (2013.01); *A61M 5/1413* (2013.01); *A61M 5/14566* (2013.01);
(Continued)

(58) Field of Classification Search
CPC .......... A61M 5/14244; A61M 5/16831; A61M 5/1413; A61M 5/14566; A61M 2205/3306; A61M 2005/16863; A61M 2205/18
See application file for complete search history.

(56) References Cited

U.S. PATENT DOCUMENTS 4,019,073 A 4/1977 Vishnevsky et al.
4,741,736 A 5/1988 Brown
(Continued)

FOREIGN PATENT DOCUMENTS

CA 2930776 C 5/2018
CN 1097632 A 1/1995
(Continued)

OTHER PUBLICATIONS

Extended European Search Report for Application No. 16837895.8, dated Nov. 7, 2018, 8 pages.
(Continued)

*Primary Examiner* — Bradley J Osinski
(74) *Attorney, Agent, or Firm* — Patterson Thuente Pedersen, P. A.

(57) ABSTRACT

Disclosed herein are systems and methods for monitoring performance of an ambulatory infusion pump. An ambulatory infusion pump can include a reservoir configured to contain a medicament including a plunger at a proximal end of the reservoir and an outlet port at a distal end of the reservoir. A motor can be configured to cause linear motion of a pushrod to contact and move the plunger to cause medicament to flow from the reservoir out of the outlet port to a patient. An optical encoder can be employed to monitor a linear position of the pushrod. In addition, the optical encoder can be employed to monitor additional system
(Continued)

conditions and/or a secondary encoder can be employed to monitor the performance of the optical encoder.

20 Claims, 13 Drawing Sheets

(51) Int. Cl.
*A61M 5/14* (2006.01)
*A61M 5/145* (2006.01)
*A61M 5/172* (2006.01)

(52) U.S. Cl.
CPC ....... *A61M 5/16831* (2013.01); *A61M 5/1458* (2013.01); *A61M 5/1723* (2013.01); *A61M 2005/16863* (2013.01); *A61M 2205/18* (2013.01); *A61M 2205/3306* (2013.01); *A61M 2205/3317* (2013.01); *A61M 2205/3569* (2013.01); *A61M 2205/502* (2013.01); *A61M 2205/8206* (2013.01)

(56) References Cited

U.S. PATENT DOCUMENTS

| | | | |
|---|---|---|---|
| 5,097,122 A | 3/1992 | Colman et al. | |
| 5,236,416 A * | 8/1993 | McDaniel | A61M 5/1456 604/67 |
| 5,795,327 A | 8/1998 | Wilson et al. | |
| 6,120,460 A | 9/2000 | Abreu | |
| 6,158,431 A | 12/2000 | Poole | |
| 6,362,591 B1 | 3/2002 | Moberg | |
| 6,413,254 B1 | 7/2002 | Hissong et al. | |
| 6,423,035 B1 | 7/2002 | Das et al. | |
| 6,468,242 B1 | 10/2002 | Wilson et al. | |
| 6,485,465 B2 | 11/2002 | Moberg et al. | |
| 6,555,986 B2 | 4/2003 | Moberg | |
| 6,659,980 B2 | 12/2003 | Moberg et al. | |
| 6,669,669 B2 | 12/2003 | Flaherty et al. | |
| 6,749,587 B2 | 6/2004 | Flaherty | |
| 6,885,881 B2 | 4/2005 | Leonhardt | |
| 6,913,933 B2 | 7/2005 | Jacobs et al. | |
| 6,918,542 B2 | 7/2005 | Silverbrook et al. | |
| 6,940,209 B2 | 9/2005 | Henderson | |
| 7,064,472 B2 | 6/2006 | Pelrine et al. | |
| 7,066,909 B1 | 6/2006 | Peter et al. | |
| 7,073,713 B2 | 7/2006 | Silverbrook et al. | |
| 7,083,108 B2 | 8/2006 | Silverbrook et al. | |
| 7,092,011 B2 | 8/2006 | Silverbrook et al. | |
| 7,097,104 B2 | 8/2006 | Silverbrook et al. | |
| 7,107,706 B1 | 9/2006 | Bailey, Sr. et al. | |
| 7,141,812 B2 | 11/2006 | Appleby et al. | |
| 7,144,384 B2 | 12/2006 | Gorman et al. | |
| 7,170,214 B2 | 1/2007 | Henderson et al. | |
| 7,187,404 B2 | 3/2007 | Silverbrook et al. | |
| 7,193,521 B2 | 3/2007 | Moberg et al. | |
| 7,201,319 B2 | 4/2007 | Silverbrook et al. | |
| 7,234,645 B2 | 6/2007 | Silverbrook et al. | |
| 7,256,824 B2 | 8/2007 | Silverbrook | |
| 7,289,142 B2 | 10/2007 | Silverbrook | |
| 7,309,943 B2 | 12/2007 | Henderson et al. | |
| 7,316,700 B2 | 1/2008 | Alden et al. | |
| 7,339,306 B2 | 3/2008 | Henderson | |
| 7,362,971 B2 | 4/2008 | Silverbrook et al. | |
| 7,373,083 B2 | 5/2008 | Silverbrook et al. | |
| 7,377,706 B2 | 5/2008 | Silverbrook et al. | |
| 7,394,182 B2 | 7/2008 | Pelrine et al. | |
| 7,411,204 B2 | 8/2008 | Appleby et al. | |
| 7,460,152 B2 | 12/2008 | Silverbrook et al. | |
| 7,464,580 B2 | 12/2008 | Zeng et al. | |
| 7,475,825 B2 | 1/2009 | Silverbrook et al. | |
| 7,483,050 B2 | 1/2009 | Silverbrook et al. | |
| 7,497,827 B2 | 3/2009 | Brister | |
| 7,517,332 B2 | 4/2009 | Tonelli et al. | |
| 7,524,045 B2 | 4/2009 | Silverbrook et al. | |
| 7,534,226 B2 | 5/2009 | Mernoe et al. | |
| 7,551,202 B2 | 6/2009 | Silverbrook | |
| 7,582,063 B2 | 9/2009 | Wurster et al. | |
| 7,621,893 B2 | 11/2009 | Moberg et al. | |
| 7,654,127 B2 | 2/2010 | Krulevitch et al. | |
| 7,704,227 B2 | 4/2010 | Moberg et al. | |
| 7,708,717 B2 | 5/2010 | Estes et al. | |
| 7,713,574 B2 | 5/2010 | Brister et al. | |
| 7,714,889 B2 | 5/2010 | Silverbrook | |
| 7,736,344 B2 | 6/2010 | Moberg et al. | |
| 7,744,589 B2 | 6/2010 | Mounce et al. | |
| 7,766,873 B2 | 8/2010 | Moberg et al. | |
| 7,774,145 B2 | 8/2010 | Brauker et al. | |
| 7,776,030 B2 | 8/2010 | Estes et al. | |
| 7,786,648 B2 | 8/2010 | Xu et al. | |
| 7,794,427 B2 | 9/2010 | Estes et al. | |
| 7,794,428 B2 | 9/2010 | Estes et al. | |
| 7,806,868 B2 | 10/2010 | De Polo et al. | |
| 7,887,512 B2 | 2/2011 | Estes et al. | |
| 7,892,206 B2 | 2/2011 | Moberg et al. | |
| 7,905,868 B2 | 3/2011 | Moberg et al. | |
| 7,922,458 B2 * | 4/2011 | Rush | F04B 49/065 417/199.2 |
| 7,935,104 B2 | 5/2011 | Yodfat et al. | |
| 7,938,803 B2 | 5/2011 | Mernoe et al. | |
| 7,944,366 B2 | 5/2011 | Krulevitch et al. | |
| 7,955,295 B2 | 6/2011 | Lee et al. | |
| 7,963,945 B2 | 6/2011 | Miller et al. | |
| 7,981,084 B2 | 7/2011 | Estes et al. | |
| 7,988,660 B2 | 8/2011 | Byland et al. | |
| 7,993,109 B2 | 8/2011 | Rush et al. | |
| 7,998,110 B2 | 8/2011 | Leung et al. | |
| 7,998,111 B2 | 8/2011 | Moberg et al. | |
| 8,062,257 B2 | 11/2011 | Moberg et al. | |
| 8,065,096 B2 | 11/2011 | Moberg et al. | |
| 8,100,852 B2 | 1/2012 | Moberg et al. | |
| 8,105,279 B2 | 1/2012 | Mernoe et al. | |
| 8,182,447 B2 | 5/2012 | Moberg et al. | |
| 8,187,228 B2 | 5/2012 | Bikovsky | |
| 8,217,533 B2 | 7/2012 | Jones et al. | |
| 8,267,893 B2 | 9/2012 | Moberg et al. | |
| 8,282,601 B2 | 10/2012 | Mernoe et al. | |
| 8,287,495 B2 | 10/2012 | Michaud et al. | |
| 8,298,184 B2 | 10/2012 | Diperna et al. | |
| 8,299,733 B2 | 10/2012 | Sattler et al. | |
| 8,304,960 B2 | 11/2012 | Sattler et al. | |
| 8,323,188 B2 | 12/2012 | Tran | |
| 8,382,703 B1 | 2/2013 | Abdelaal | |
| 8,414,563 B2 | 4/2013 | Kamen et al. | |
| 8,450,905 B2 | 5/2013 | Guidarelli et al. | |
| 8,466,637 B2 | 6/2013 | Guidarelli et al. | |
| 8,517,991 B2 | 8/2013 | Clemente | |
| 8,562,590 B2 | 10/2013 | Yodfat et al. | |
| 8,573,027 B2 | 11/2013 | Rosinko et al. | |
| 8,641,671 B2 | 2/2014 | Michaud et al. | |
| 8,758,323 B2 | 6/2014 | Michaud et al. | |
| 8,926,561 B2 | 1/2015 | Verhoef et al. | |
| 8,986,253 B2 | 3/2015 | Diperna | |
| 9,180,243 B2 | 11/2015 | Michaud | |
| 9,211,377 B2 | 12/2015 | Diperna et al. | |
| 9,362,851 B2 | 6/2016 | Xu et al. | |
| 9,421,329 B2 | 8/2016 | Kruse | |
| 9,555,186 B2 | 1/2017 | Kruse | |
| 9,675,756 B2 | 6/2017 | Kamen | |
| 9,962,486 B2 | 5/2018 | Rosinko et al. | |
| 9,993,595 B2 | 6/2018 | Michaud et al. | |
| 10,010,674 B2 | 7/2018 | Rosinko et al. | |
| 10,279,106 B1 | 5/2019 | Cook et al. | |
| 10,279,107 B2 | 5/2019 | Michaud | |
| 10,357,603 B2 | 7/2019 | Michaud et al. | |
| 10,850,032 B2 | 12/2020 | Steck et al. | |
| 2003/0060768 A1 | 3/2003 | Kiyatake et al. | |
| 2003/0163090 A1 | 8/2003 | Blomquist et al. | |
| 2004/0204673 A1 | 10/2004 | Flaherty | |
| 2004/0220551 A1 | 11/2004 | Flaherty et al. | |
| 2005/0010980 P1 | 1/2005 | Inoue et al. | |
| 2005/0020980 A1 | 1/2005 | Inoue et al. | |
| 2005/0177111 A1 | 8/2005 | Ozeri et al. | |
| 2006/0049720 A1 | 3/2006 | Henderson et al. | |
| 2007/0062250 A1 | 3/2007 | Krulevitch et al. | |

(56) References Cited

U.S. PATENT DOCUMENTS

| | | | |
|---|---|---|---|
| 2007/0093753 A1* | 4/2007 | Krulevitch | A61M 5/16831 604/131 |
| 2007/0149926 A1 | 6/2007 | Moberg et al. | |
| 2007/0156092 A1 | 7/2007 | Estes et al. | |
| 2007/0167905 A1 | 7/2007 | Estes et al. | |
| 2007/0173762 A1 | 7/2007 | Estes et al. | |
| 2007/0270750 A1 | 11/2007 | Dacquay | |
| 2008/0045902 A1 | 2/2008 | Estes et al. | |
| 2008/0045903 A1 | 2/2008 | Estes et al. | |
| 2008/0045904 A1 | 2/2008 | Estes et al. | |
| 2008/0045931 A1 | 2/2008 | Estes et al. | |
| 2008/0051697 A1 | 2/2008 | Mounce et al. | |
| 2008/0051698 A1 | 2/2008 | Mounce et al. | |
| 2008/0051709 A1 | 2/2008 | Mounce et al. | |
| 2008/0051711 A1* | 2/2008 | Mounce | A61M 5/1413 604/131 |
| 2008/0051716 A1 | 2/2008 | Stutz | |
| 2008/0051727 A1 | 2/2008 | Moberg et al. | |
| 2008/0097291 A1 | 4/2008 | Hanson et al. | |
| 2008/0097375 A1 | 4/2008 | Bikovsky | |
| 2008/0097381 A1 | 4/2008 | Moberg et al. | |
| 2008/0125700 A1 | 5/2008 | Moberg et al. | |
| 2008/0215035 A1 | 9/2008 | Yodfat et al. | |
| 2008/0221523 A1 | 9/2008 | Moberg et al. | |
| 2009/0036870 A1 | 2/2009 | Mounce et al. | |
| 2009/0124994 A1 | 5/2009 | Roe | |
| 2009/0157003 A1 | 6/2009 | Jones | |
| 2009/0192724 A1 | 7/2009 | Brauker et al. | |
| 2009/0270811 A1 | 10/2009 | Mounce et al. | |
| 2010/0037680 A1 | 2/2010 | Moberg et al. | |
| 2010/0078017 A1* | 4/2010 | Andrieux | A61M 16/161 128/200.24 |
| 2010/0121169 A1 | 5/2010 | Petisce et al. | |
| 2010/0152674 A1 | 6/2010 | Kavazov et al. | |
| 2010/0179402 A1 | 7/2010 | Goode, Jr. et al. | |
| 2010/0185142 A1 | 7/2010 | Kamen et al. | |
| 2010/0185175 A1 | 7/2010 | Kamen et al. | |
| 2010/0198183 A1 | 8/2010 | Lanigan et al. | |
| 2010/0211003 A1 | 8/2010 | Sundar | |
| 2010/0217192 A1 | 8/2010 | Moberg et al. | |
| 2010/0217193 A1 | 8/2010 | Moberg et al. | |
| 2010/0249706 A1 | 9/2010 | Clemente | |
| 2010/0324398 A1 | 12/2010 | Tzyy-Ping | |
| 2011/0054390 A1 | 3/2011 | Searle et al. | |
| 2011/0092948 A1 | 4/2011 | Shachar et al. | |
| 2011/0144586 A1 | 6/2011 | Michaud et al. | |
| 2011/0144616 A1 | 6/2011 | Michaud et al. | |
| 2011/0152770 A1 | 6/2011 | Diperna et al. | |
| 2011/0152824 A1 | 6/2011 | Diperna et al. | |
| 2011/0152827 A1 | 6/2011 | Wiegel et al. | |
| 2011/0160654 A1 | 6/2011 | Hanson et al. | |
| 2011/0166544 A1 | 7/2011 | Verhoef et al. | |
| 2011/0190614 A1 | 8/2011 | Brister et al. | |
| 2011/0190694 A1 | 8/2011 | Lanier, Jr. et al. | |
| 2011/0213329 A1 | 9/2011 | Yodfat et al. | |
| 2011/0257895 A1 | 10/2011 | Brauker et al. | |
| 2012/0029433 A1 | 2/2012 | Michaud et al. | |
| 2012/0029468 A1 | 2/2012 | Diperna | |
| 2012/0030610 A1 | 2/2012 | Diperna et al. | |
| 2012/0041387 A1* | 2/2012 | Bruggemann | A61M 5/14546 604/218 |
| 2012/0078216 A1 | 3/2012 | Smith et al. | |
| 2012/0096954 A1 | 4/2012 | Vazquez et al. | |
| 2012/0172817 A1 | 7/2012 | Brueggemann et al. | |
| 2012/0192951 A1 | 8/2012 | Yodfat et al. | |
| 2012/0259282 A1 | 10/2012 | Alderete, Jr. | |
| 2013/0053816 A1 | 2/2013 | Diperna et al. | |
| 2013/0150766 A1 | 6/2013 | Olde | |
| 2013/0204542 A1 | 8/2013 | Olde | |
| 2013/0324928 A1 | 12/2013 | Kruse | |
| 2013/0331790 A1 | 12/2013 | Brown et al. | |
| 2014/0039392 A1 | 2/2014 | Geipel et al. | |
| 2014/0054883 A1 | 2/2014 | Lanigan et al. | |
| 2014/0276423 A1 | 9/2014 | Lecanu-Fayet | |
| 2015/0174320 A1 | 6/2015 | Grant | |
| 2015/0202375 A1* | 7/2015 | Schabbach | A61M 5/24 604/207 |
| 2016/0051758 A1 | 2/2016 | Rosinko et al. | |
| 2016/0082186 A1 | 3/2016 | Rosinko et al. | |
| 2016/0136357 A1 | 5/2016 | Yang | |
| 2016/0157759 A1 | 6/2016 | Yang | |
| 2016/0157765 A1 | 6/2016 | Zhu | |
| 2016/0158436 A1 | 6/2016 | Yang | |
| 2016/0199572 A1 | 7/2016 | Yang | |
| 2016/0339172 A1 | 11/2016 | Michaud et al. | |
| 2017/0049957 A1 | 2/2017 | Michaud | |
| 2017/0056581 A1 | 3/2017 | Deak et al. | |
| 2018/0071454 A1 | 3/2018 | Betts et al. | |
| 2018/0264189 A1 | 9/2018 | Michaud et al. | |
| 2018/0333543 A1* | 11/2018 | Diaz | A61M 5/3202 |
| 2019/0255248 A1 | 8/2019 | Michaud | |
| 2019/0321546 A1 | 10/2019 | Michaud et al. | |

FOREIGN PATENT DOCUMENTS

| | | |
|---|---|---|
| CN | 1611001 A | 4/2005 |
| CN | 101189431 A | 5/2008 |
| CN | 101563120 A | 10/2009 |
| CN | 103228303 A | 7/2013 |
| CN | 101745163 B | 12/2013 |
| CN | 103768679 A | 5/2014 |
| DE | 102015104786 A1 | 9/2016 |
| EP | 2420274 A1 | 2/2012 |
| EP | 2510960 A1 | 10/2012 |
| WO | WO-0228532 A2 | 4/2002 |
| WO | WO-2008024808 A2 | 2/2008 |
| WO | WO-2008024812 A2 | 2/2008 |
| WO | WO-2009013736 A1 | 1/2009 |
| WO | WO-2009016636 A2 | 2/2009 |
| WO | WO-2010096449 A2 | 8/2010 |
| WO | WO 2016/061194 A1 | 4/2016 |

OTHER PUBLICATIONS

International Preliminary Report on Patentability for Application No. PCT/US2016/047725, dated Mar. 1, 2018, 8 pages.
International Search Report and Written Opinion for Application No. PCT/US2016/047725, dated Nov. 28, 2016, 12 pages.
International Search Report and Written Opinion for Application No. PCT/US2019/016466, dated May 22, 2019, 13 pages.
Application and File history for U.S. Appl. No. 16/403,016, filed May 3, 2019. Inventors: Michaud.
Application and File history for U.S. Appl. No. 15/241,257, filed Aug. 19, 2016. Inventors: Michaud.
Office Action dated Dec. 11, 2019 for Chinese Application No. 201680061057.X, 17 pages.
Communication dated Feb. 17, 2020 for EP Application 16837895. 8, 5 pages.
Chinese Application No. 2019800235332, Search Report dated Oct. 24, 2021, 3 pages.

* cited by examiner

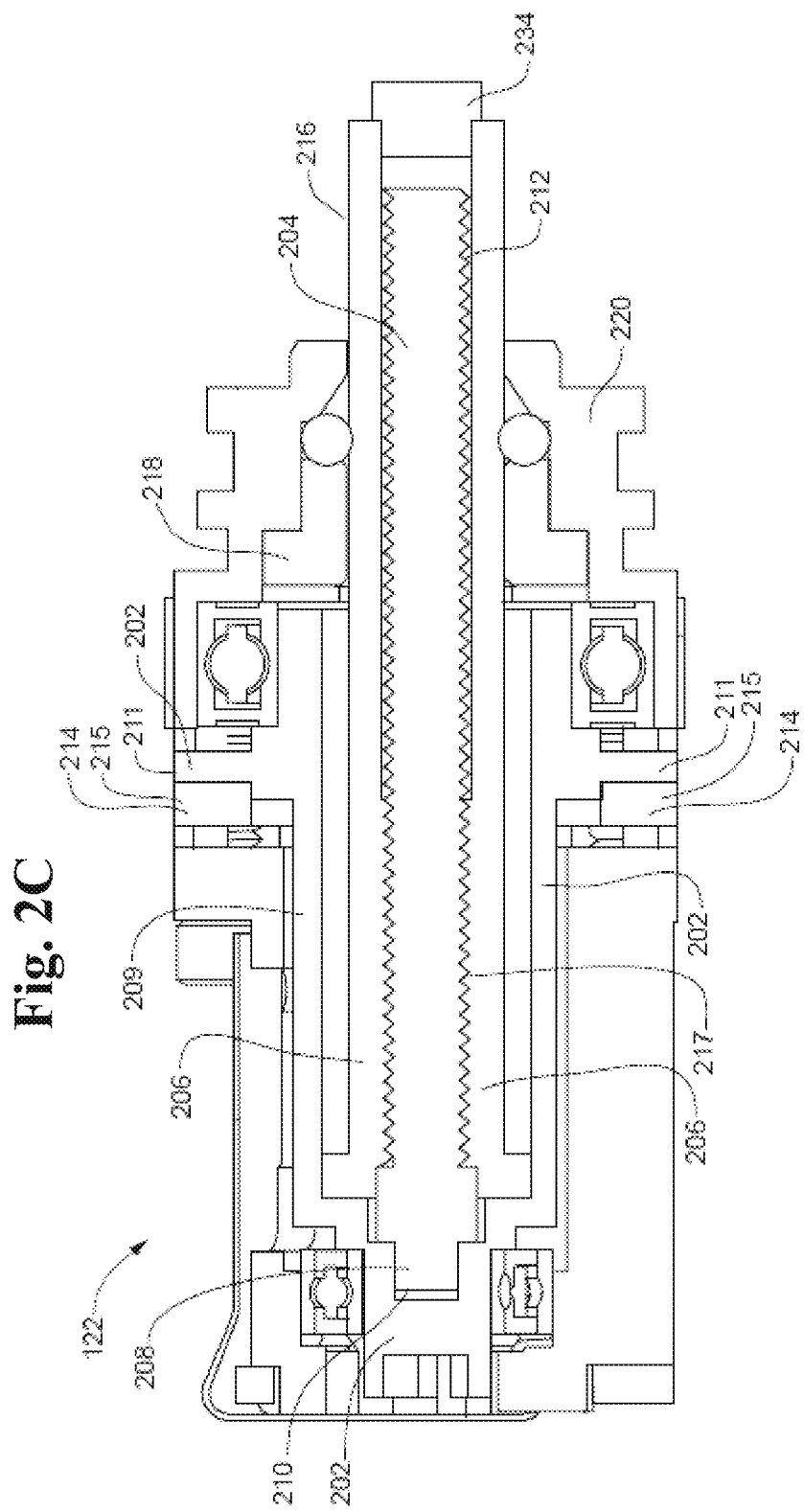

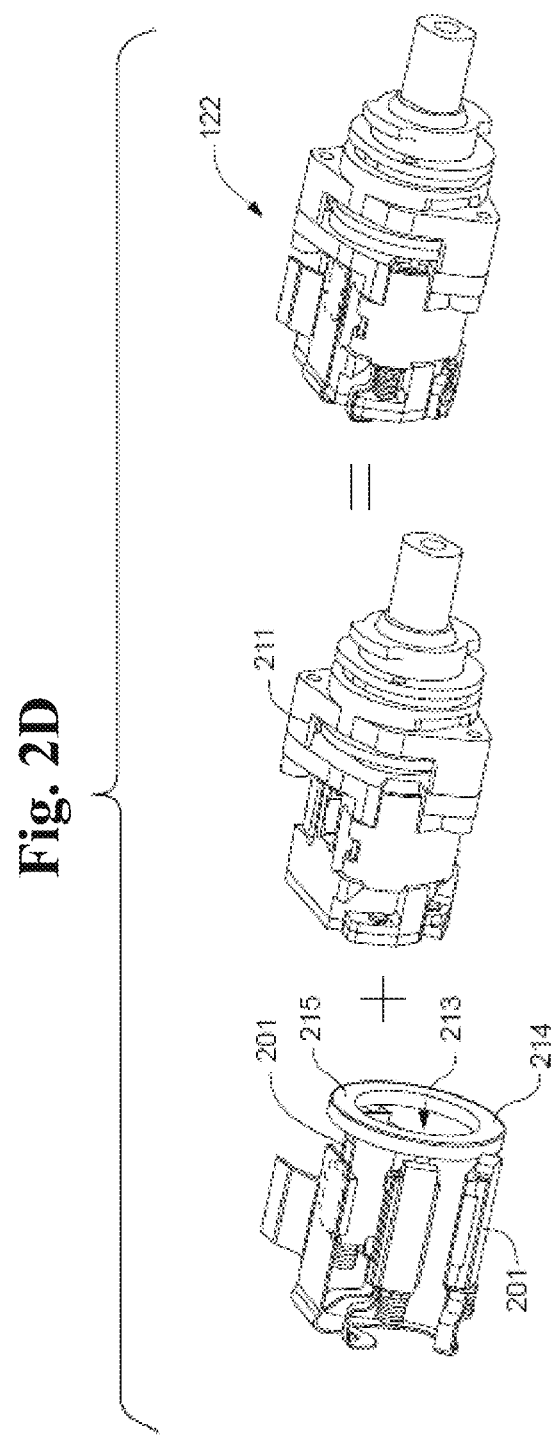

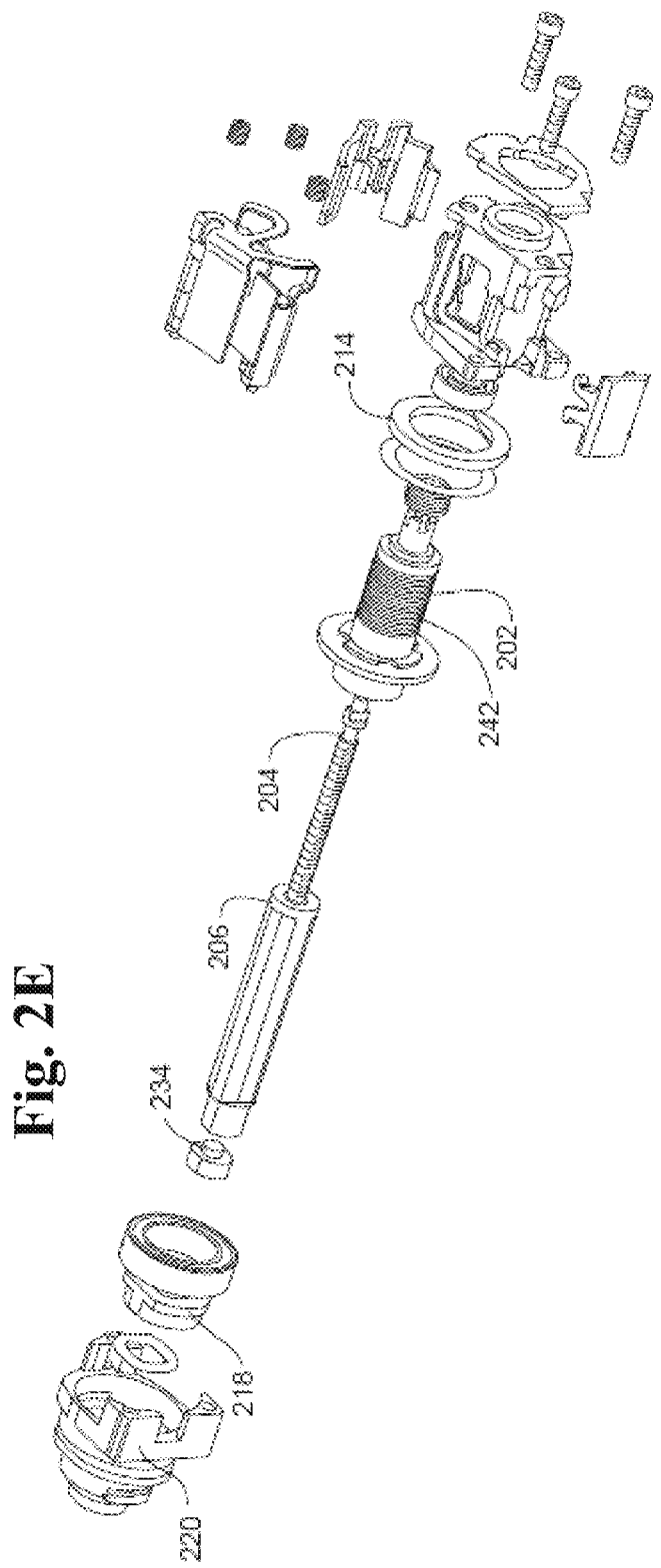

METHODS AND SYSTEMS FOR DETECTING INFUSION PUMP CONDITIONS

RELATED APPLICATIONS

The present application claims the benefit of U.S. Provisional Application No. 62/626,430 filed Feb. 5, 2018 and U.S. Provisional Application No. 62/632,294 filed Feb. 19, 2018, each of which is hereby incorporated herein in its entirety by reference.

TECHNICAL FIELD

The present invention relates to medical pumps for delivering medicament to a patient and, more specifically, to user-wearable infusion pumps for delivering medicament such as insulin to a patient.

BACKGROUND

There are many applications in academic, industrial, and medical fields that benefit from devices and methods that are capable of accurately and controllably delivering fluids, such as liquids and gases, that have a beneficial effect when administered in known and controlled quantities. Such devices and methods can be particularly useful in the medical field where treatments for many patients include the administration of a known amount of a substance at predetermined intervals.

One category of devices for delivering such fluids is that of pumps that have been developed for the administration of insulin and other medicaments for those suffering from both Type 1 and Type 2 diabetes. Some pumps configured as portable infusion devices can provide continuous subcutaneous medicament injection and/or infusion therapy for the treatment of diabetes. Such therapy may include, e.g., the regular and/or continuous injection or infusion of insulin into the skin of a person suffering from diabetes and offer an alternative to multiple daily injections of insulin by an insulin syringe or an insulin pen. Such pumps can be ambulatory/portable infusion pumps that are worn by the user and may use replaceable cartridges. Examples of such pumps and various features that can be associated with such pumps include those disclosed in U.S. Patent Application Publication No. 2013/0053816; U.S. Pat. Nos. 8,573,027; 8,986,253; U.S. Patent Application Publication No. 2013/0324928; U.S. Patent Application Publication No. 2013/0331790; U.S. Pat. No. 8,287,495; U.S. Patent Publication No. 2017/0049957; and U.S. Patent Publication No. 2016/0339172, each of which is hereby incorporated herein by reference in its entirety.

One common type of ambulatory infusion pump utilizes an electromagnetic motor to rotate a lead screw that drives a syringe to cause medicament to be delivered from a medicament reservoir in the pump to a patient. Most such systems incorporate a gear reduction system to decrease the speed generated by the motor in order to increase the torque on the lead screw to a sufficient level to cause the medicament to be dispensed. Such systems generally employ a force sensor for detecting and monitoring pressure conditions in the syringe cartridge. However, this additional sensor requires additional space and electronics and represents an additional possible failure point in a complex electromechanical system.

Another type of ambulatory infusion pump that has been developed utilizes piezoelectric elements to rotate a lead screw and drive a syringe that causes medicament to be delivered. One such pump, further details of which can be found in U.S. Patent Publication No. 2017/0049957 assigned to the assignee of the present application, does not requires a gear reduction system in order to drive the syringe. Therefore, this type of pump requires fewer parts and can be made smaller than pumps that utilize gear reduction systems. This type of pump can also employ an encoder system. The encoder system may in one example utilize an optical encoder integrated circuit that monitors markings configured radially around an outer surface of a cylindrical drive element in order to monitor a rotational position of the drive element.

SUMMARY

Disclosed herein are systems and methods for monitoring performance of an ambulatory infusion pump. An ambulatory infusion pump can include a reservoir configured to contain a medicament including a plunger at a proximal end of the reservoir and an outlet port at a distal end of the reservoir. A motor can be configured to cause linear motion of a pushrod to contact and move the plunger to cause medicament to flow from the reservoir out of the outlet port to a patient. An optical encoder can be employed to monitor a linear position of the pushrod. In addition, the optical encoder can be employed to monitor additional system conditions and/or a secondary encoder can be employed to monitor the performance of the optical encoder.

In embodiments, systems and methods for monitoring and detecting pressure conditions in a syringe-based infusion pump without the use of a separate force sensor are disclosed herein. In an infusion pump that employs a piezoelectric motor to rotate a lead screw without a gear reduction system and that utilizes an encoder for monitoring a position of the lead screw, the encoder can further be utilized to detect pressure conditions in the system. As pressure in the system increases, the torque required to rotate the lead screw increases which causes the time it takes for a rotational displacement of a give size to occur to be longer. By monitoring the time required for a given rotational displacement to occur, it is possible to detect high or low pressure conditions in the cartridge.

In embodiments, systems and methods for monitoring performance of a primary encoder used to provide feedback regarding operation of a user-wearable infusion pump by monitoring markings on a rotationally driven element of the pump are disclosed herein. Such a primary encoder operates relative to the markings and in some embodiments is powered on and off within, e.g., a single revolution of the drive element to, e.g., reduce power consumption. As such, the encoder may drift slightly when power-cycled. In addition, the optical properties of such an encoder system, wear, contamination, and other factors may contribute to errors in which the encoder does not perform as intended. Such performance problems may be manifested by the system missing an encoder "count" or registering extra or unexpected "counts" that cannot be identified with use of the primary encoder alone. To address such possibilities, a secondary encoder, such as a magnetic encoder, can be used in conjunction with such pump systems to monitor rotation of the rotationally driven element to verify that the primary encoder is tracking correctly by comparing the amount of rotation determined by the primary encoder to the amount detected by the secondary encoder. Systems incorporating such designs enable extremely low power operation while still guaranteeing the primary encoder maintains sufficient position information.

In one embodiment, a secondary encoder for monitoring performance of a primary encoder of an infusion pump can include a magnetic sensor and a magnet. The magnet can be disposed on the same rotationally driven element monitored by the primary encoder and the magnetic sensor, by sensing the magnet, can monitor the number of revolutions of the rotary element during various pump operations. The system can compare the detected number of revolutions to the number of revolutions detected by the primary encoder. If the number of revolutions detected by each encoder is the same, then no further action needs to be taken and the pump can proceed with normal pump operation. If the numbers are not the same, it may be indicative of an error in operation of the primary encoder.

In another embodiment, a secondary encoder for monitoring performance of a primary encoder of an infusion pump can include a magnetic sensor and a magnet. The magnet can be disposed on the same rotationally driven element monitored by the primary encoder and the magnetic sensor, by sensing the magnet, can monitor an amount of rotation of the rotary element during various pump operations. The system can compare the detected number of encoder counts (e.g., markings detected by the primary encoder) to an expected number or range of numbers of encoder counts based on the amount of rotation detected by the magnetic encoder. If the number of counts is the expected number or within the expected range, then no further action needs to be taken and the pump can proceed with normal pump operation. If the numbers are not the same or within an expected range, it may be indicative of an error in operation of the primary encoder.

In one embodiment, an ambulatory infusion pump system includes a reservoir configured to contain a medicament including a plunger at a proximal end of the reservoir and an outlet port at a distal end of the reservoir, a pushrod, and a motor configured to cause linear motion of the pushrod. The pump can further include an optical encoder configured to monitor a linear position of the pushrod. A processor can be configured to control the motor and pushrod to cause delivery of medicament from the reservoir by causing the pushrod to contact and move the reservoir plunger. The processor can command the motor to actuate to deliver medicament from the reservoir by advancing the pushrod from a first linear position to a second linear position and monitor a move completion time for the pushrod to advance from the first linear position to the second linear position. The processor can compare the move completion time to an expected move completion time and notify a user of an error if the monitored move completion time is longer than the expected move completion time. In one or more embodiments, the optical encoder monitors the linear position of the pushrod by monitoring markings on a rotating drive tube that causes linear motion of the pushrod when it is rotated.

In one embodiment an ambulatory infusion pump system includes a reservoir configured to contain a medicament including a plunger at a proximal end of the reservoir and an outlet port at a distal end of the reservoir, a pushrod, a drive tube including a plurality of markings configured to cause linear motion of the pushrod when the drive tube is rotated and a motor configured to cause the drive tube to rotate to cause linear motion of the pushrod to contact and move the plunger to cause medicament to flow from the reservoir out of the outlet port to a patient. The system can further include an optical encoder configured to monitor a linear position of the pushrod by sensing the markings on the drive tube when the drive tube is rotated. A magnetic sensor can further be included and be configured to monitor rotation of the drive tube by sensing a magnet disposed on the drive tube when the drive tube is rotated. In one or more embodiments, performance of the optical encoder can be monitored by comparing the rotation of the drive tube as monitored by the optical encoder with the rotation as monitored by the magnetic sensor.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which:

FIGS. 2A-2E depict a pump system according to an embodiment of the invention.

Figure 1A:
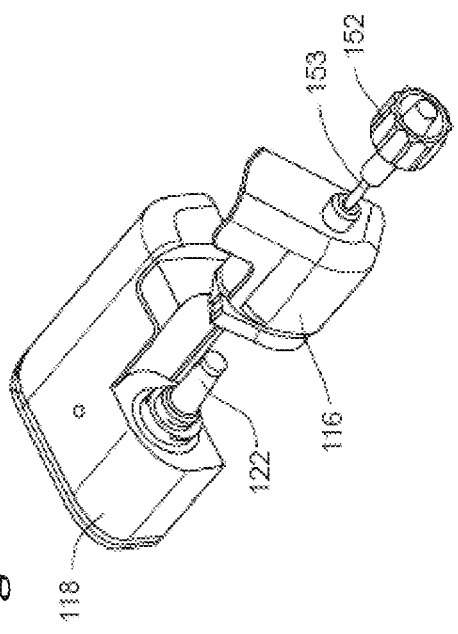
FIGS. 1A-1C depict a pump system according to an embodiment of the invention.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Figure 1C:
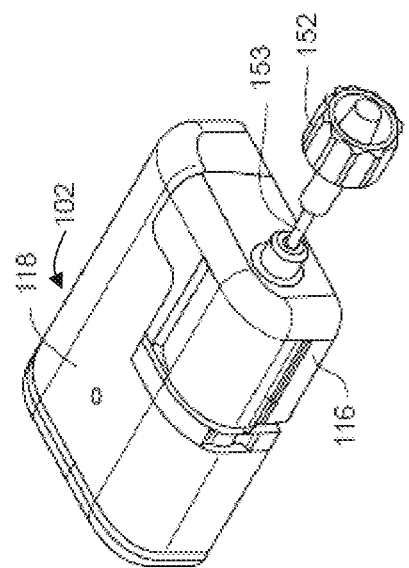
Figure 1B:
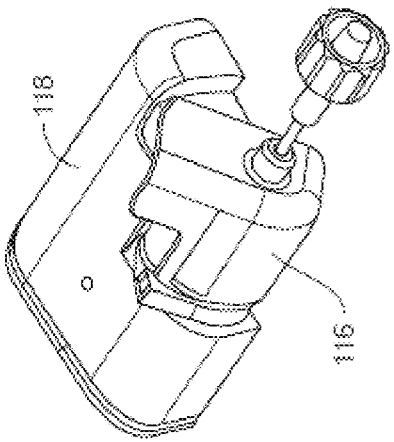
Figure 2A:
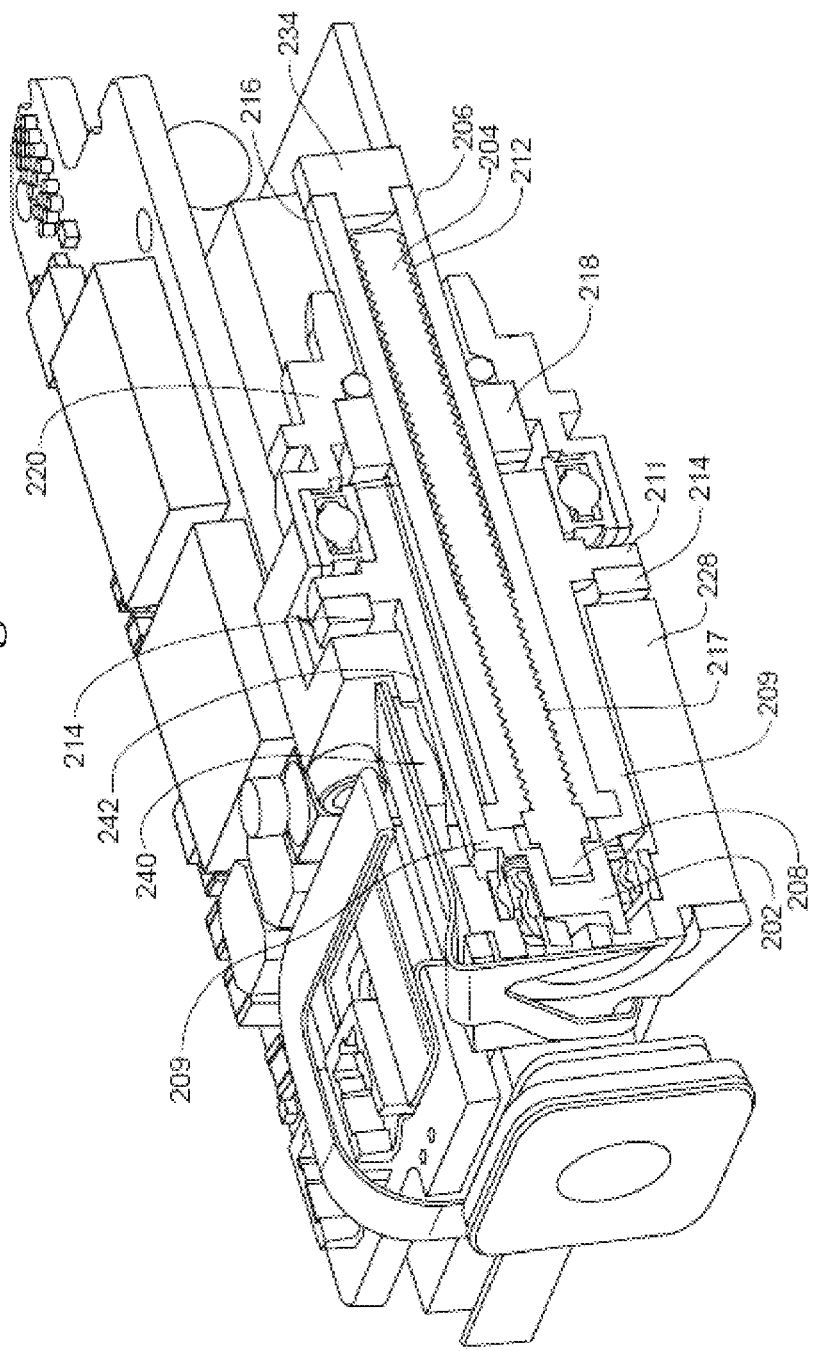
Figure 2B:
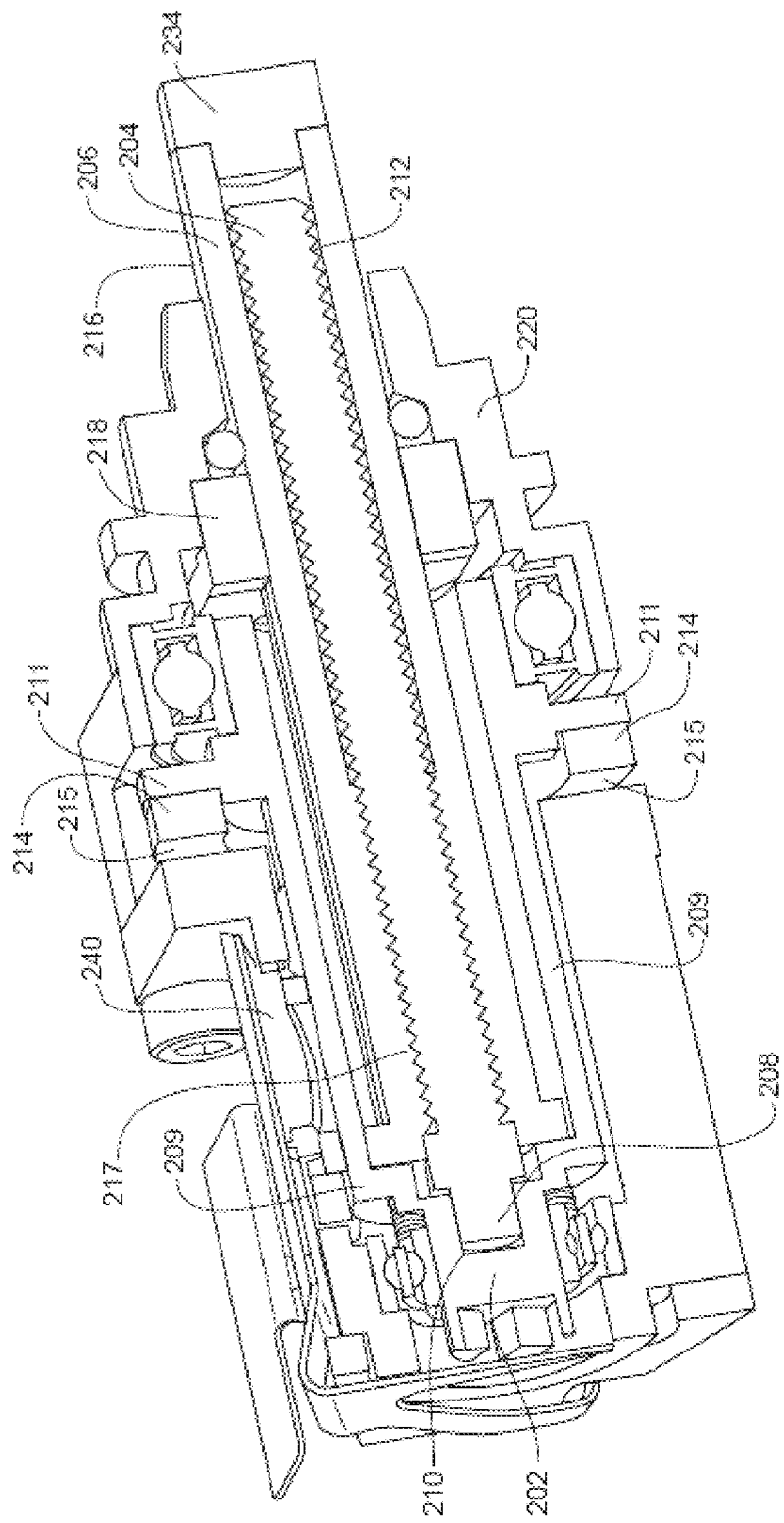

FIGS. 1A-1C depict a pump system including a pump 102 according to an embodiment of the invention. Drive unit 118 of pump 102 includes a drive mechanism 122 that mates with a recess in a disposable cartridge 116 of pump 102 to attach the cartridge 116 to the drive unit 118 and provide for delivery of medicament such as insulin from the cartridge 116 to a user through a cannula. A pump system according to embodiments of the present invention can include a pump 102 including a drive unit 118 and a cartridge 116 as well as any additional components, such as for example, an infusion set. A short length of tubing 153 can extend from cartridge 116 with a connector 152 designed to attach to a corresponding connector of such an infusion set that includes a length of tubing extending from the corresponding connector to an infusion site having an infusion site connector to deliver medicament to the infusion site. Further details regarding such pumps can be found in U.S. patent application Ser. No. 14/707,851 filed May 8, 2015 and U.S. Patent Publication Nos. 2016/0339172 and 2017/0049957, each of which is hereby incorporated herein by reference in its entirety.

In one embodiment, pump 102 includes a processor that controls operations of the pump and, in some embodiments, may communicate in either one-way or two-way modes to, e.g., receive commands and/or other signals, including data, from a separate device and/or, e.g., to send signals, including data, to a separate device. Such a separate device can include, for example, a dedicated remote control or a smartphone or other consumer electronic device executing an application configured to enable the device to transmit operating commands to the processor of pump 102. In some embodiments, processor can also transmit information to one or more separate devices, such as information pertaining to device parameters, alarms, reminders, pump status, etc. Such communications between (and among) the one or more devices and pump may be one-way or two-way for, e.g., effective transfer of data among the devices and the pump, control of pump operations, updating software on the devices and/or pump, and allowing pump-related data to be viewed on the devices and/or pump.

FIGS. 2A-2E depict a drive mechanism 122 that utilizes piezoelectricity to dispense medicament from a cartridge in an ambulatory infusion pump system. In general, drive mechanism 122 includes a plurality of piezoelectric elements that when energized with a drive signal oscillate against a drive disk to induce rotational motion of the drive disk. The rotational motion of the drive disk is converted to linear motion of a pushrod that interfaces with a syringe in the cartridge to advance the syringe and dispense medicament.

The primary elements of the motor assembly utilized to translate the rotational motion of a ceramic drive disk 214 induced by the motors 201 into linear motion include a drive tube 202, a lead screw 204 and a drive nut or pushrod 206. As can be most clearly seen in FIGS. 2A-2C, the ceramic drive disk 214 is coupled to the drive tube 202 with a body 209 of the drive tube 202 extending through an opening 213 in the ceramic drive disk 214 and the body 215 of the ceramic drive disk 214 abutting a flange 211 of the drive tube 202. This interconnection of the ceramic drive disk 214 and drive tube 202 causes rotation of the ceramic drive disk 214 to induce rotation of the drive tube 202. A proximal end 208 of the lead screw 204 is received within and coupled to a recess 210 in the drive tube 202, such that rotation of the drive tube 202 also rotates the lead screw 204. An internally threaded portion 217 of the pushrod 206 is coupled with external threads 212 of the lead screw 204. The external perimeter 216 of the pushrod 206 can be non-circular and slidably mated with a guide bushing 218 coupled to and contained within a front housing 220 to prevent the push rod 206 from rotating. This in turn enables rotation of the lead screw 204 to effect linear motion of the push rod 206. The push rod 206 is therefore contained within and directly driven by the motor assembly. A drive tip 234 can be attached to a distal end of the pushrod 206.

In one embodiment, operation of the unit is accomplished by energizing the piezoelectric motors with an electrical drive signal to cause them to oscillate against the ceramic drive disk 214. This oscillation induces rotational motion of the ceramic drive disk 214. Rotational motion of the ceramic drive disk 214 causes the drive tube 202 and the lead screw 204 to rotate. The intermeshing threaded exterior portion 212 of the lead screw 204 and interior threaded portion 217 of the pushrod 206 along with the non-circular perimeter 216 of the pushrod 206 that is constrained from rotating by the guide bushing 218 cause this rotational motion to be converted into linear motion of the pushrod 206. When the drive mechanism 122 is attached to a cartridge containing medicament, such as cartridge 116, the linear motion of the pushrod 206 causes the drive tip 234 of the pushrod to advance a syringe in the cartridge to cause medicament to be dispensed from the cartridge. Further details regarding such a drive system can be found in U.S. Patent Publication No. 2017/0049957, previously incorporated herein by reference.

Figure 3B:
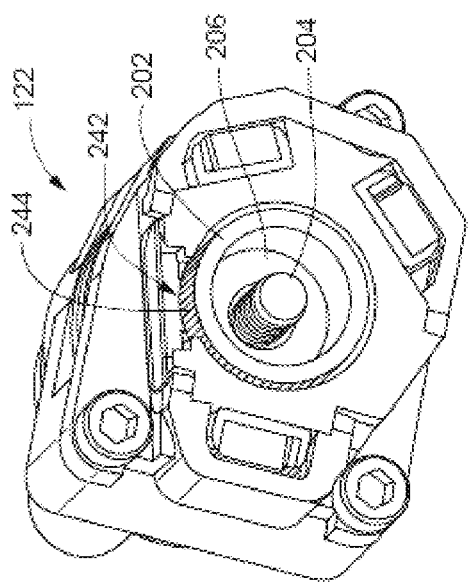
FIGS. 3A-3C depict a pump system according to an embodiment of the invention.
Figure 3C:
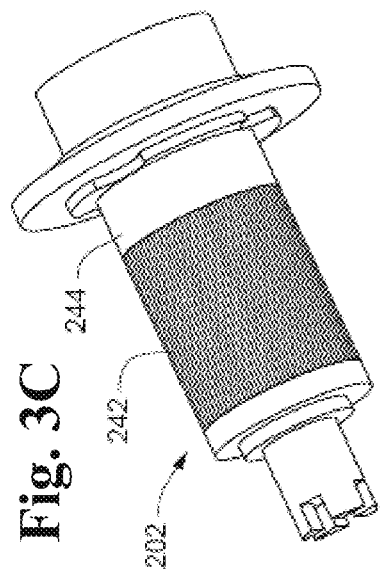
Figure 3A:
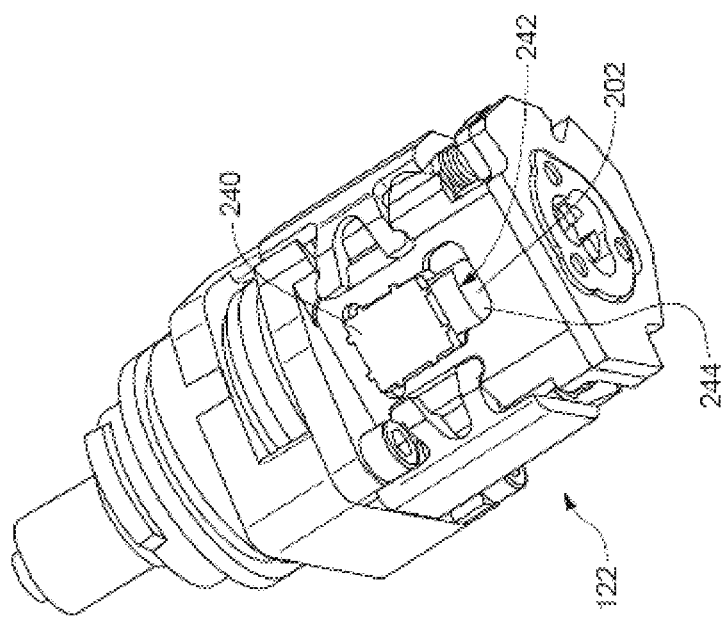

An additional feature that can be utilized by a drive mechanism according to embodiments of the present invention is an optical encoder system. Referring to FIGS. 3A-3C, the device according to one embodiment can include an optical encoder integrated circuit 240 configured to monitor markings 242 radially around an outer perimeter surface 244 of the drive tube 202 (note that FIG. 3B depicts a drive mechanism embodiment with certain rear portions of the device removed and FIG. 3C depicts only drive tube 202, both for sake of clarity). The optical encoder integrated circuit 240 can include a reflective optical encoder with an integrated light source. The light source can be positioned above the markings 242 on the drive tube 202, which such markings can be, e.g., a pre-defined series of reflective and non-reflective lines. By tracking the series of lines as the drive tube 202 is rotated, the integrated circuit monitors a rotational position of the drive tube 202, which indicates a linear position of the pushrod 206. Although described herein with respect to drive tube 202, it should be understood that encoder 240 could be utilized to monitor markings on any rotationally-driven element that is rotated to cause delivery of medicament with a pump.

In one embodiment, the optical encoder system can monitor three output channels that are indicated by the markings 242 on the drive tube 202. These can include, for example, an A channel, a B channel and an index channel. Monitoring of the A channel and the B channel can be used by the system to determine the rotational position, speed, and direction of rotation of the drive tube.

Monitoring of the index channel can serve a number of purposes. For example, the index channel can be configured such that one index channel pulse is expected for a set number of A and B pulses. If that index channel pulse is not detected after the set number of A and B pulses, it can be inferred that the encoder system may not be operating properly, and one or more signals can be sent to a processor or other device to disable the drive system, send a warning or other message to a user, etc. Similarly, this configuration can be used to determine if the drive tube moved when the encoder system was not turned on. Generally speaking, this may occur because, in an effort to save battery power, the encoder is only turned on right before a motor move and then turned off shortly after the move is complete. As such, if some fault (e.g., hardware fault, cosmic ray, etc.) causes the drive tube to rotate when the encoder is power off, it cannot be determined from monitoring only the A and B channels. Comparing the index pulse signal to the A and B signals enables detection of such fault conditions. This configuration can further be used to determine if the A and B channels are operating as expected; if so, one index pulse should be received for each set number of A and B pulses as noted above. In the described optical encoder system, the markings 242 that are monitored are provided on a component of the system, drive tube 202, that otherwise serves an additional functional purpose (rotating the lead screw).

Systems as described herein generally include a normal amount of "slippage" during normal load conditions. Slippage occurs between the drive tip and the drive disk and refers to kinetic energy from the motion of the drive tip that is converted to heat instead of motion of the drive disk. This includes startup slippage due to inertia and steady state slippage due to rotational resistance from a variety of sources (e.g., ball bearing friction, bushing friction, and axial load on the drive nut from the cartridge plunger friction). At startup (e.g., when the motor is first energized), the drive tip oscillates at a certain speed and this movement reaches steady state almost instantaneously, but the inertia of the drive disk and drive tube assembly prevents the drive disk-drive tube assembly from matching that very high acceleration, which results in the startup slippage. During steady state conditions (constant rotational speed) there is slippage due to the fact that there is an imperfect frictional connection between the drive tip and the drive disk and as the load increases, slippage increases and more of the kinetic energy from the motion of the drive tip is converted to heat instead of motion of the drive disk.

Encoder system can also be used indirectly to, e.g., monitor pressure in the pump. In one embodiment, as pressure in cartridge 116 increases, more force is required to advance the syringe and push rod 206, and accordingly the torque required to rotate the lead screw 204 increases. In turn, the amount of slippage, as described above, between the piezoelectric motors 201 and the drive disk 214 increases to greater than the normal amount due to this increased torque level. This increase in slippage causes a rotational displacement of the marked drive tube 202 and lead screw 204 of a given amount to take a longer amount of time. By monitoring the time required for a given rotational displacement to occur, high force and low force conditions on the cartridge syringe and push rod 206 due to pressure in the pump can be determined. This enables one or more pump-related conditions to be detected, including the presence or absence of occlusion, the presence or absence of a cartridge, general performance and health of the drive system of the pump, etc. The pump can include an internal timer that the processor uses to determine the move completion time. Monitoring of pump conditions in this manner can be done by the processor within the pump described above. Alternatively, a separate device, such as a dedicated remote control or a smartphone, can receive data relating to the encoder from the pump processor, monitor the data, and make determinations relating to pump conditions. Such data may also be recorded into memory of the pump and/or a separate device and analyzed further using diagnostic tools such as may reside on a server, diagnostic and/or repair equipment, etc.

By way of example only (as such times can vary significantly depending on a particular design configuration), typical move completion times for the drive tube and lead screw to rotate a given distance during normal system operations (when the pushrod is advancing the cartridge syringe to dispense medicament) may be in a range of about 20 milliseconds to about 40 milliseconds. When move completion times for the given distance are longer than about 40 milliseconds, this may indicate there is additional slippage in the system because not all of the piezoelectric energy is being converted to rotational motion of the drive disk and drive tube—and corresponding linear motion of the pushrod. The processor then can infer that one or more of a number of conditions in the system, such as those discussed above, may be present. Similarly, there may be situations where no rotational movement is detected. Such a situation may indicate that enough of the piezoelectric energy is being lost in slippage such that the pushrod has not linearly advanced at all in the time period observed/monitored. Thus, while the system is generally referred to herein as detecting "move completion time", it should be understood that in circumstances where no movement is detected, there is no actual movement and the move completion time instead refers to reaching a threshold period of time wherein the lack of movement indicates a system condition.

When no rotational movement is detected, meaning that an insufficient amount of piezoelectric energy is being converted to effectuate the desired degree of rotational movement of the drive disk, the processor can infer that one or more of several conditions may be present in the system. Such conditions include, for example, that the drive system is stuck, that the cartridge is empty and/or that the pushrod has reached its full travel state. The condition of the system can be determined by the processor based on the position of the pushrod relative to the fully retracted and/or full extended states of the pushrod as indicated by the encoder system and the amount of medicament that the system has calculated as is remaining in the reservoir. If the pushrod is in its fully extended state, then no further rotational movement indicates that the pushrod has reached its fully extended travel state. If the pushrod is not fully extended, the condition of the system can be determined based on the amount of medicament that the processor has tracked as remaining in the reservoir. If the processor has determined that only a small amount of medicament is remaining in the reservoir, such as, for example, 5 to 10 units of medicament or less, but there is no rotational motion of the drive tube when the motor is actuated, the system can infer that the cartridge is empty. If there is no rotational motion but the processor has determined that a significant amount of medicament, such as, for example 100 units of medicament, is remaining in the cartridge, the processor can infer that the drive system is stuck.

When the drive tube is rotating such that the pushrod is moving linearly upon motor actuation, but the move completion time is longer than expected, this may indicate that a high pressure condition exists in the system, such as an occlusion in the fluid line. For example, if there is an expected move completion time of between about 20 ms to about 40 ms, a move completion time of about 50 ms can cause the processor to infer that there is an occlusion, and any number of actions optionally may be taken as a result thereof and as described below.

Figure 4A:
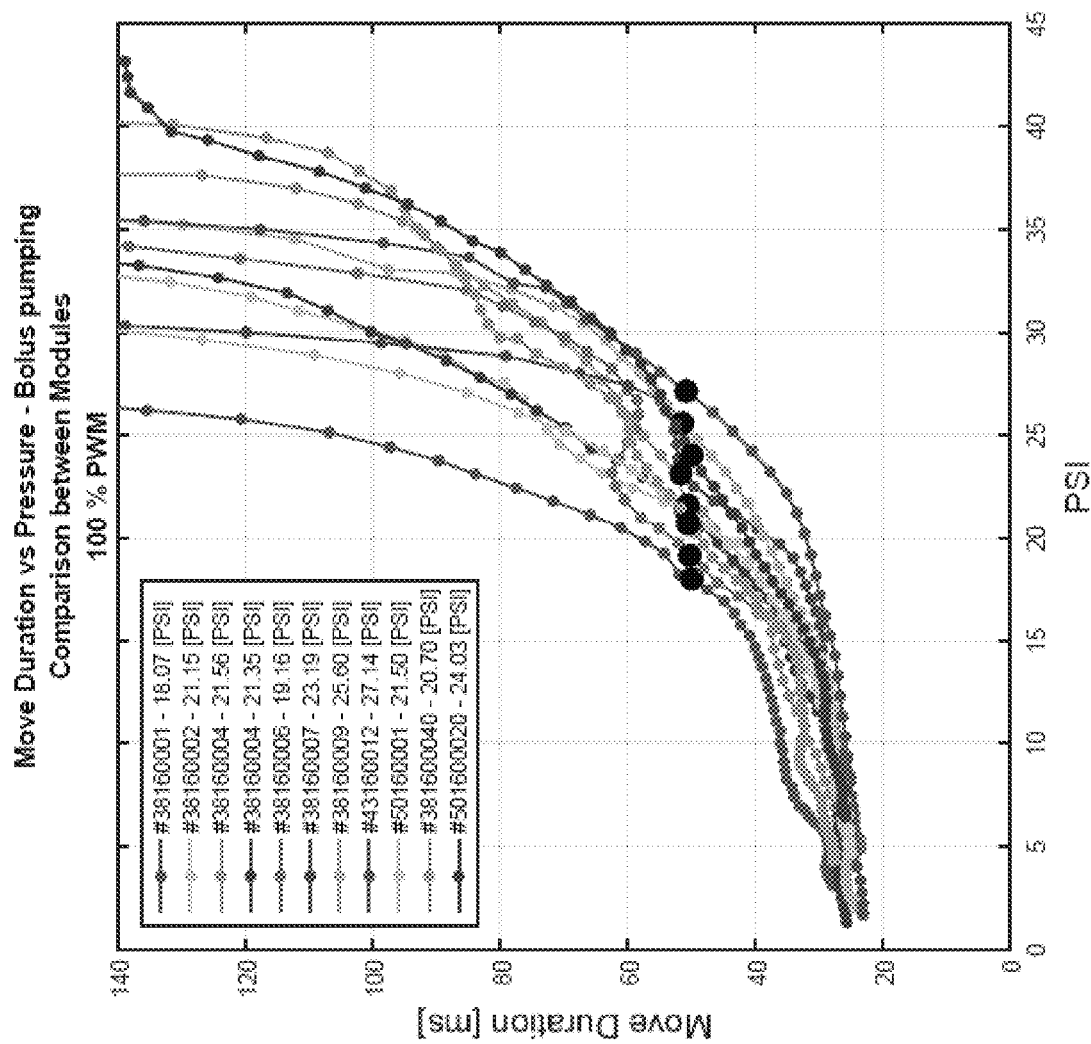
FIGS. 4A-4B depict occlusion detection data.
Figure 4B:
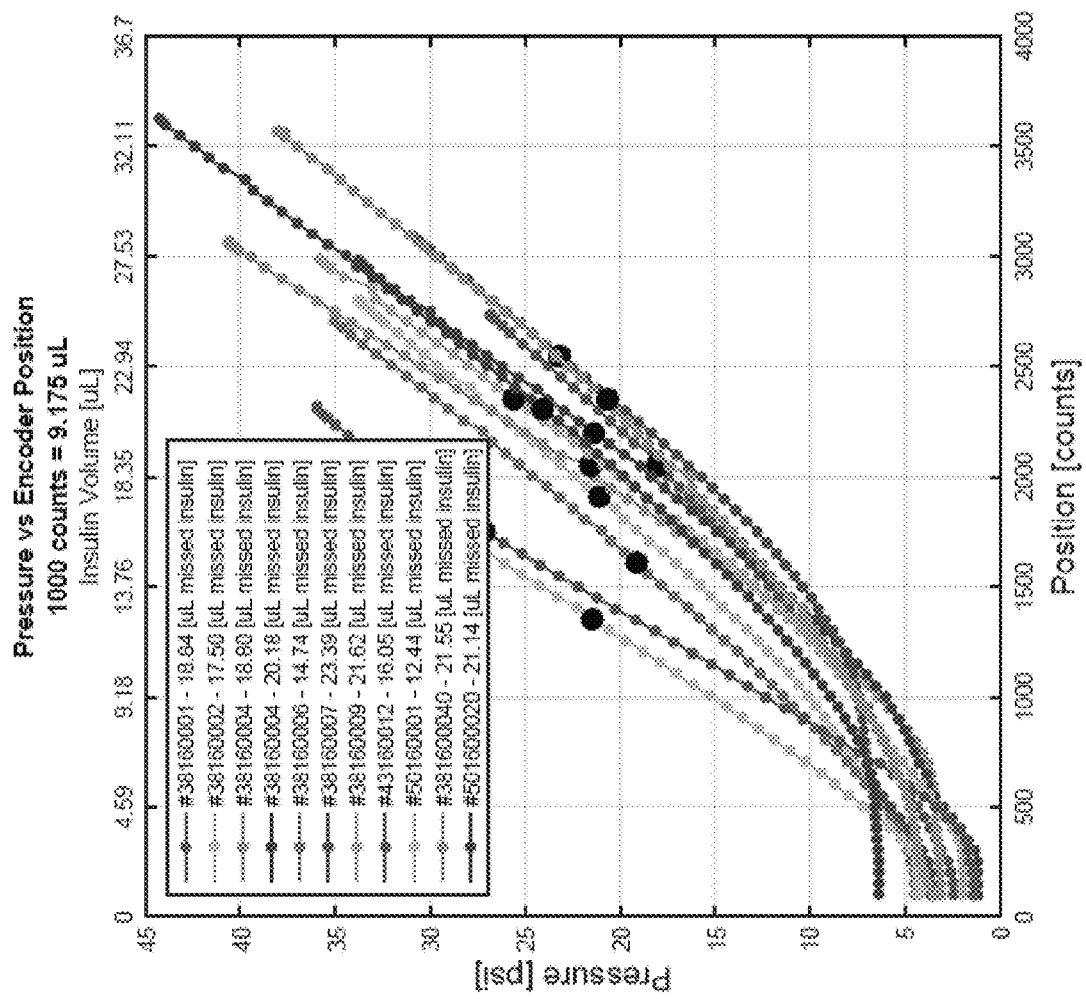

FIGS. 4A-4B depict occlusion detection testing data. Specifically, the data show how an embodiment of the pump systems described herein responds after clamping the pump's infusion set tubing to simulate an occlusion. FIG. 4A depicts move duration or completion time in milliseconds (y-axis) as a function of pressure in the pump in pounds per square inch (x-axis). FIG. 4B depicts the same testing data with pressure in the pump as a function of encoder position in counts (e.g., number of markings on the drive tube). As can be seen in FIG. 4A, as pressure in the pump increases, there is an increase in the time it takes for the drive tube to move or rotate a given distance. Each smaller dot 10 represents a sequential 50-count move. The larger dots 12 correspond to 50-count moves that took approximately 50 ms to complete. This 50 ms threshold correlated to a range of pressure in the pump of around 18 psi to around 27 psi. Because the fluid cartridge and infusion set tubing is not a perfectly rigid system, when an occlusion occurs the drive tube may still rotate and the pushrod may still translate to pump medicament out, but instead of the medicament being delivered to the patient the system will flex as the fluid pressure increases. The encoder positioning depicted in FIG. 4B can be used to determine the amount of medicament that was not delivered prior to the occlusion being detected. As can be seen in FIG. 4B, in the tested data a range of about 12 microliters of insulin and about 23 microliters of insulin went undelivered due to the detected occlusions.

The time it takes for a given rotational displacement to occur can also be monitored to detect low pressure conditions. As discussed above, rotation of the lead screw 204 causes linear motion of the pushrod 206 such that a drive tip 234 of the pushrod contacts and advances a syringe in the cartridge to cause medicament to be dispensed from the cartridge 116. There is accordingly a level of force exerted on the pushrod from the cartridge syringe during normal system operations. If the pushrod is not in contact with the syringe, this force is not present which will lead to lower move completion times. For example, if typical move completion times when the pump is dispensing medicament are between about 20 and about 40 milliseconds, move completion times less than about 20 ms can indicate that the pushrod is not in contact with the syringe. This could indicate that the cartridge is not present (which would be visually apparent) and can also be used during priming of the cartridge during initial use following a cartridge fill to determine when the pushrod has contacted the syringe plunger. The ability to determine that the pushrod is not in contact with the cartridge syringe also provides an additional safety feature because it indicates that the pump may not be dispensing medicament when the motors are actuated.

The system can take various actions based on detected system conditions. The system can provide an alarm or alert related to a detected condition on a user interface of the pump and/or on a user interface of a remote control device, such as a dedicated remote control or a smartphone. Such alarms or alerts may also include an auditory and/or vibratory alert. For example, if the system has determined that an occlusion is present, an occlusion alarm can be issued. Such an alert may notify the user that an occlusion has been detected and instruct the user to clear the occlusion. In some embodiments, the user can enter a troubleshooting mode through the alarm that provides instructions and/or suggestions for clearing the occlusion (or other condition). The user may be able to acknowledge and clear the alarm. If the occlusion was not properly remedied prior to clearing the alarm, the system will again detect the occlusion and provide another alarm. A corresponding alert or alarm can be provided for other detected system conditions in a similar manner, such as the cartridge being empty or missing, the drive system being stuck, and the pushrod having reached the end of its travel. In some embodiments, when the occlusion or other system condition alarm is issued, the system also automatically ceases medicament delivery until the alarm is cleared.

Figure 5:
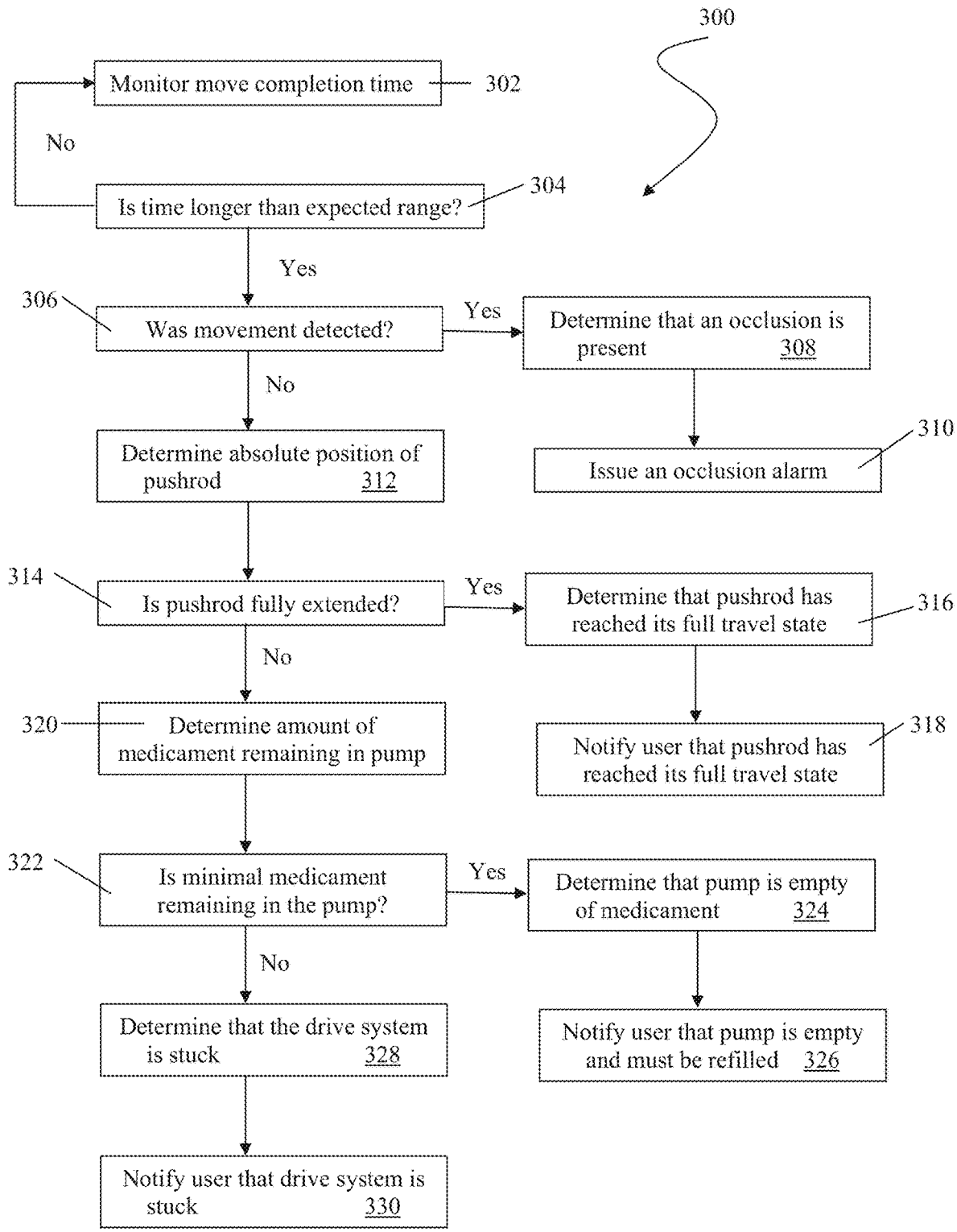
FIG. 5 depicts flow chart of a method of monitoring system conditions of an infusion pump according to an embodiment of the invention.

FIG. 5 depicts a flowchart of method steps for monitoring system conditions 300 in an infusion pump as described herein. At step 302, move completion times of a given rotational distance are monitored and it is determined if each completion time is in an expected range at step 304. If the time is within the expected range, the method continues monitoring move completion times at step 302. If the time is longer than the expected range, it is then determined at step 306 if movement was detected during the monitoring time period. If movement was detected—meaning that the drive tube rotated as expected but the movement took longer than expected—then the system determines that an occlusion is present at step 308 and an occlusion alarm can be issued at step 310.

Still referring to FIG. 5, if rotational movement was not detected during the monitoring period, the system next determines the position of the pushrod as indicated by the encoder system at step 312. If the position of the pushrod is determined to be fully extended at step 314, the system can determine that the pushrod has reached its full travel state at step 316 and the user may be notified at step 318. The drive system would then need to be reset in order for more medicament to be delivered. If the pushrod has not reached its full travel state, the system then determines an estimate of the amount of medicament remaining in the pump at step 320. If the system estimates that only a minimal amount of medicament remains in the pump at step 322, such as, for example, between about 5 and about 10 units of medicament or less, at step 324 the system determines that the pump is considered empty of medicament and can notify the user that the pump is considered to be empty at step 326 and that the pump cartridge needs to be refilled or replaced. If the system estimates that a higher amount of medicament remains in the pump, then the system determines that the drive system is stuck at step 328 and the user can be notified at step 330 that the drive system is stuck and, e.g., the system should be inspected.

The system can be adjusted to modify a sensitivity setting for the various alerts and alarms described herein in various embodiments of the invention. As discussed above, typical move completion times in the system may be in the range of about 20 to about 40 milliseconds. The alarm sensitivity can be adjusted by changing the amount of time a move must take before an alarm is triggered. For example, in one embodiment as discussed above an alarm is triggered when a move completion time is 50 milliseconds or longer. To increase the alarm sensitivity, the alarm time threshold could be decreased to 40 milliseconds. Similarly, the alarm sensitivity can be decreased by increasing the alarm time threshold, such as, for example, to about 60 milliseconds. In addition, detection thresholds could be set based on the characteristics of a given drive system to account for system-to-system variability such that each system could have a different move duration threshold to decrease the variation across systems in the amount of missed medicament when an occlusion is detected.

Figure 6:
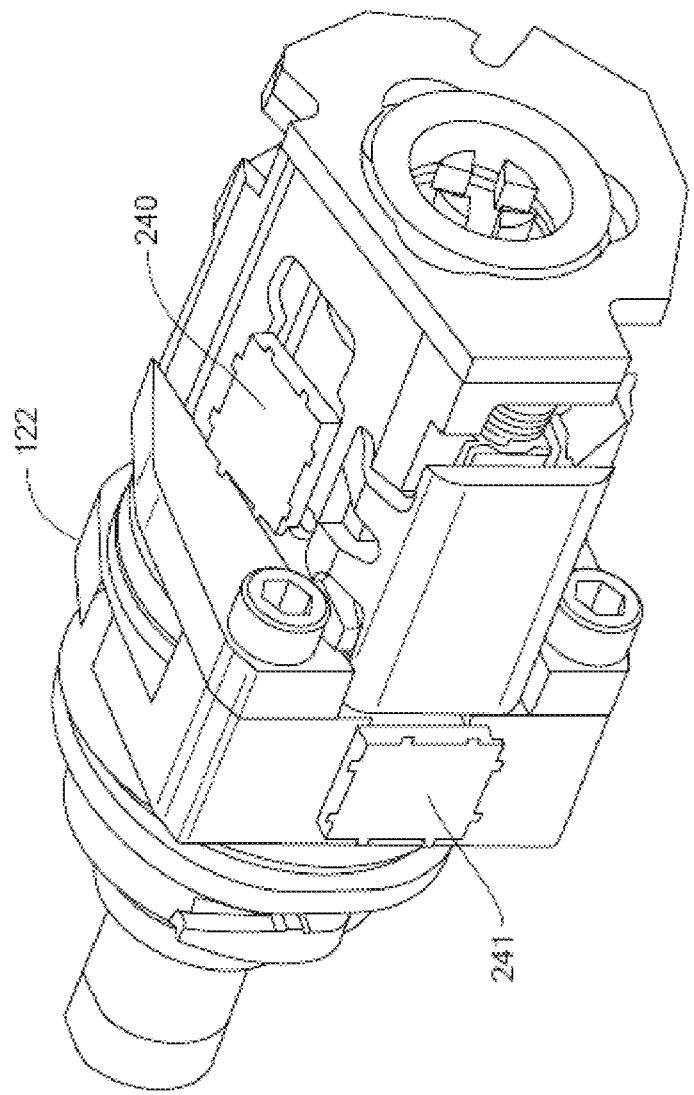
FIG. 6 depicts a pump system according to an embodiment of the invention.

As disclosed in U.S. Patent Publication No. 2017/0049957, in some embodiments an ambulatory infusion pump can include a second encoder 241 in addition to primary encoder 240. In one embodiment, the second encoder 241 can be positioned as shown in FIG. 6 to also monitor markings on the drive tube. In such an embodiment, the drive tube 202 may include a second set of optical markings for monitoring by the second encoder 241 in addition to the markings 242 discussed with respect to FIGS. 3A-3C. Utilization of a pair of encoders 240, 241 enables signal redundancy to prevent a single encoder fault from causing over delivery of medicament. Alternatively, instead of a second optical encoder, the second encoder could be a magnetic encoder, a Hall effect encoder, or other type of encoder as known in the art.

Figure 7:
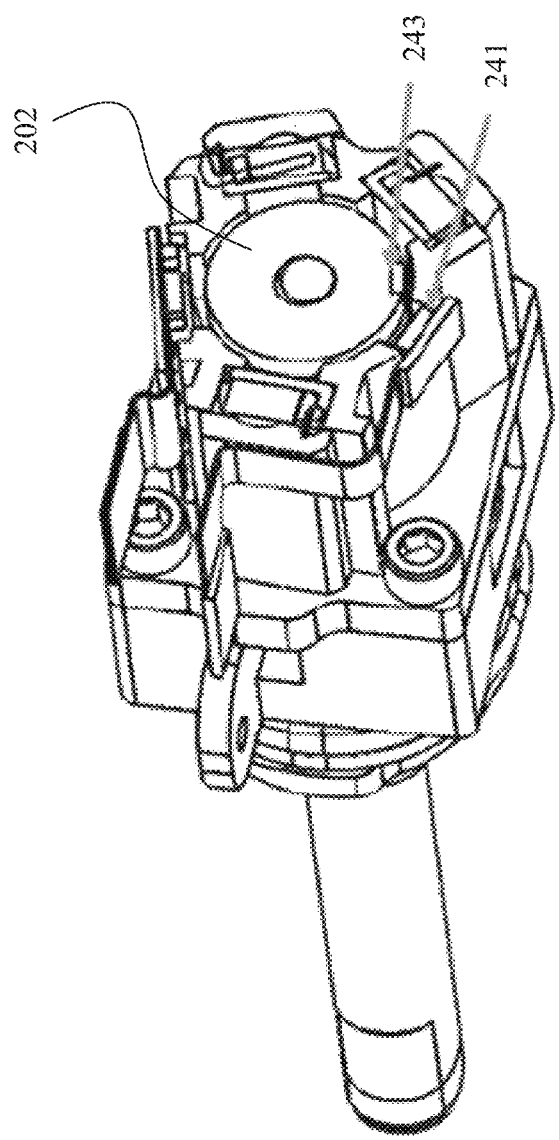
FIG. 7 depicts a pump system according to an embodiment of the invention.

In some embodiments, second encoder can be a magnetic sensor used to monitor the primary encoder performance by providing input to an algorithm for monitoring the performance of the primary encoder. Referring to FIG. 7, magnetic sensor 241 can be a Hall effect magnetic sensor that senses a magnet 243 disposed on the drive tube 202 or other rotatable element. In other embodiments, the magnetic sensor can be a reed switch. As the drive tube 202 rotates, the magnet 243 will rotate with it. Each time the magnet 243 passes the magnetic sensor 241, the sensor will detect the magnet 243 such that the processor of the device can further track system conditions with the information from magnetic sensor 243. Although depicted as employing a single magnet 243, in various embodiments two or more magnets can be arranged at regular or irregular intervals around the drive tube 202. Such a system would cause the magnetic sensor 241 to be triggered more than once each revolution of the drive tube 202, increasing the sensitivity of the system to any primary encoder 240 errors.

Because the primary encoder 240 operates relative to the markings 242, it can drift slightly when power off or power cycled to reduce the power consumption of pump. Encoder 240 can also experience other problems—as previously described—each of which could contribute to one or more performance errors and/or other problems. Therefore, as noted above, in various embodiments, secondary encoder 241 can be used to monitor performance of the primary encoder 240 to ensure that the primary encoder is properly tracking the rotational position and speed of the drive tube 202. Such a system is useful in detecting primary encoder system failures in order to prevent such failures from leading to delivery errors, which can lead to serious medical consequences for patients. Use of a magnetic encoder system as described herein therefore enables encoder monitoring with extremely low power operation.

In one embodiment, magnetic sensor 241 can monitor primary encoder 240 performance during cartridge 116 changing, pump priming or other operations that involve use of the motors 201 to effect rewinding or extending of the leadscrew 204. The magnetic sensor 241, by sensing the magnet 243, can monitor the number of revolutions of the drive tube 202 during one or more of the above procedures and compare the detected number of revolutions to the number of revolutions detected by the primary encoder 240. If the number of revolutions detected by each encoder is the same, then no further action needs to be taken and the pump can proceed with normal pump operation. If the numbers are not the same, it may be indicative of an error in operation of the primary encoder and an alarm or alert can be issued to notify the user of the error.

If an error is detected in operation of the primary encoder, one or more signals may be sent to a processor to disable the drive system. The user may optionally be notified, e.g., that the drive system has been automatically disabled, to request a user confirmation to disable the drive system, etc. In some embodiments, the system may automatically, or by user prompt, run one or more self-tests to confirm the error. Such a self-test may involve, e.g., retracting the lead screw, operating the motors and comparing secondary magnetic and primary optical encoder readings and/or confirming that the magnetic detection(s) were from the magnet and not a false detections that could be triggered by, e.g., an external force not related to the drive system. In some embodiments, if the error is confirmed, if an error is detected in embodiments that do not automatically self-test to confirm the error, the user can be instructed to return the pump to the manufacturer and/or contact the manufacturer to, e.g., obtain a replacement.

Magnetic sensor 241 can also be utilized to monitor primary encoder 240 performance during normal pumping operations, e.g., when delivering medicament to a patient with the pump. As discussed above, primary encoder 240 monitors a plurality of markings 242, or counts, on the drive tube 202 during device operation. During routine medicament delivery, the number of monitored counts in a given time period corresponds with an amount of medicament delivered over the time period. It is therefore important that the number of encoder counts is properly and accurately measured by the primary encoder. When magnetic sensor 241 is triggered, the number of encoder counts as measured by primary encoder 240 can be compared to a target number or range of encoder counts that are expected to have occurred. For example, in the embodiment employing one magnet 243 on drive tube 202, the drive tube 202 will have undergone one complete revolution each time magnetic sensor 241 is triggered. The number of encoder counts measured by the primary encoder can therefore be compared to an expected number or range of encoder counts and if the number is the same as the expected number or within the expected range, pumping operations can continue uninterrupted. If not, the user can be notified of the error and/or the drive system disabled as described above. Such an error may occur due to the primary encoder being turned off and on within a given revolution such that it is possible for counts to be missed or for extra counts to occur.

In addition to or alternatively to monitoring and comparing the number of discrete encoder counts, the magnetic sensor 241 can be used to determine whether the number of complete revolutions of the drive tube 202 measured by the primary encoder 241 during normal pumping operations is accurate. The drive tube 202 in a pump as described herein may undergo a number of complete revolutions to deliver the medicament contained in a given cartridge. A further check on the performance of the primary encoder can therefore be to compare the number of complete revolutions of drive tube 202 as measured by the primary encoder to the number of revolutions determined by the magnetic sensor 241. For example, in the embodiment where there is one magnet 243 that therefore triggers the magnetic sensor 241 once a at a single absolute position each revolution, the number of times that the magnetic sensor has been triggered can be compared to the number of revolutions measured by the primary encoder 243. In embodiments employing more than one magnetic sensor a different number of magnetic sensor triggers will equal a complete revolution to be compared to the primary encoder, or a smaller revolution amount can be monitored and compared, such as, for example, half revolutions. If the number of revolutions determined by the primary encoder and the magnetic encoder is the same, pumping operations can continue uninterrupted. If not, the user can be notified of the error and/or the drive system disabled as described above.

A magnetic encoder can further be used to monitor primary encoder 240 performance during a user-initiated or automatic self-test of the system. No medicament is delivered by the system as the test is conducted solely for the purpose of testing the performance of the primary encoder, regardless of the presence or absence of an internal and/or user-facing (e.g., graphical user interface on the pump or remote device, via vibratory and/or audible means, etc.) indication of an error or other prompting. Such a test can otherwise be conducted similarly to the encoder monitoring described above during normal pump operations, with the number of counts and/or revolutions determined by the primary encoder 240 compared to a number or range of expected counts and/or revolutions as monitored by the magnetic encoder system.

Figure 8:
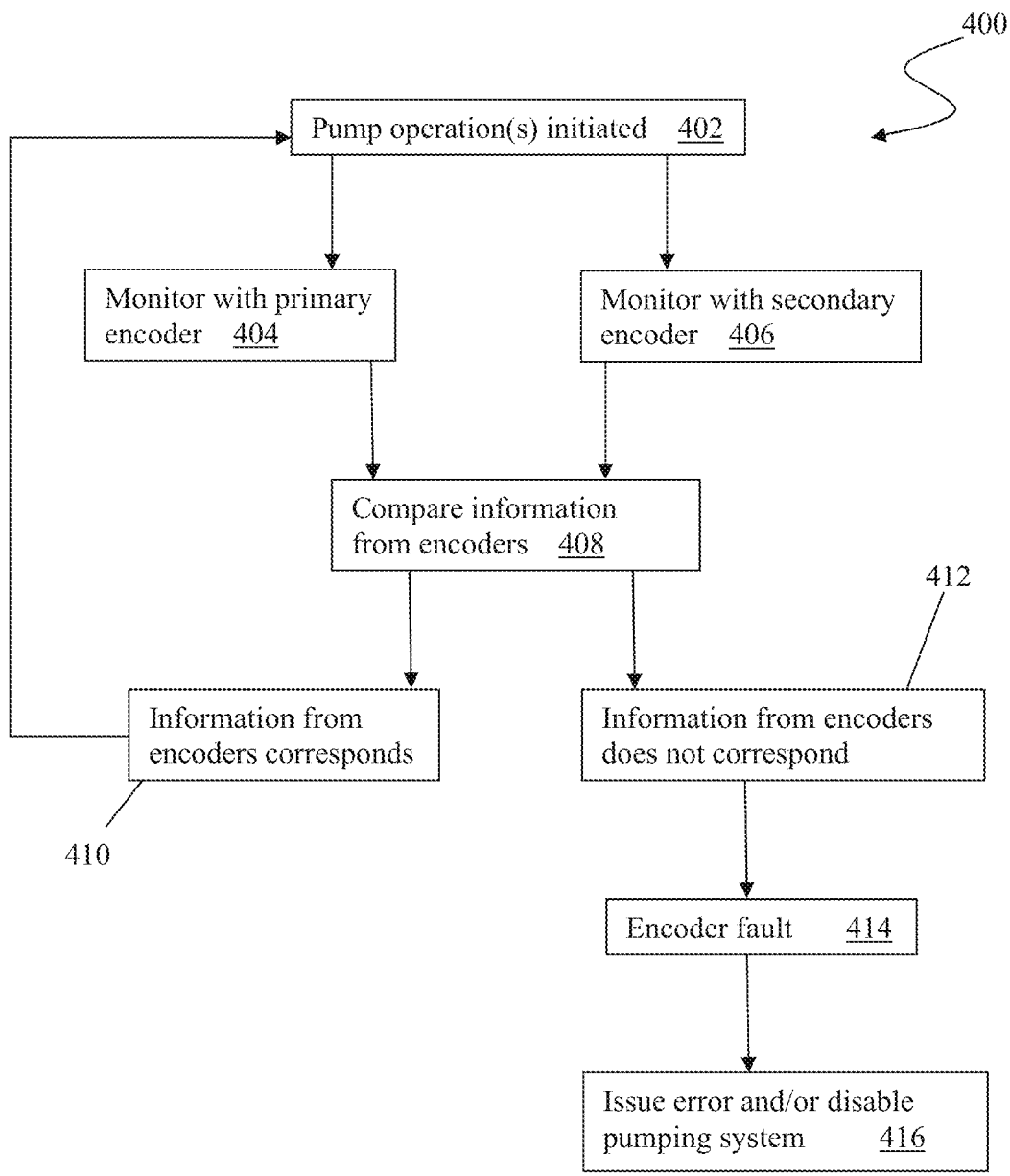
FIG. 8 depicts a flowchart of a method for monitoring encoder performance in a user-wearable infusion pump according to an embodiment of the invention.

Referring now to FIG. 8, a flowchart depicting steps 400 for monitoring the performance of a primary encoder in an ambulatory infusion pump is depicted. At step 402, one or more pump operations are initiated, such as, for example, normal pump operations, a cartridge change, a self-test, etc. as described above. At steps 404 and 406, the rotational position of the drive tube or other rotationally driven element of the system is monitored with the primary encoder 240 and the second encoder 241, respectively. As described above, in various embodiments primary encoder 240 may be an optical encoder that monitors markings 242 on the drive tube 202 and secondary encoder 241 may be magnetic sensor that detects a magnet 243 on the drive tube 202. At step 408, the information detected by the two encoders is compared as described herein. If at step 410 the comparison indicates that the information from the encoders corresponds with each other, such as, for example, a number of revolutions measured by each encoder matching and/or or a number of encoder counts measured by the primary encoder matching or being within a target range when the magnetic sensor is triggered, pumping operations continue. If the comparison indicates that the information from the encoders does not correspond with each other at step 412, an encoder fault is determined by the processor at step 416. One or more error messages can then be issued and/or the pumping system can then be disabled at step 414 as described above.

Also incorporated herein by reference in their entirety are commonly owned U.S. Pat. Nos. 8,287,495; 8,408,421 8,448,824; 8,573,027; 8,650,937; 8,986,523; 9,173,998; 9,180,242; 9,180,243; 9,238,100; 9,242,043; 9,335,910; 9,381,271; 9,421,329; 9,486,171; 9,486,571; 9,492,608; 9,503,526; 9,555,186; 9,565,718; 9,603,995; 9,669,160; 9,715,327; 9,737,656; 9,750,871; 9,867,937; 9,867,953; 9,940,441; 9,993,595; 10,016,561 and 10,201,656. commonly owned U.S. Patent Publication Nos. 2009/0287180; 2012/0123230; 2013/0053816; 2014/0276419; 2014/0276420; 2014/0276423; 2014/0276569; 2014/0276570; 2015/0182693; 2016/0082188; 2017/0049957; 2017/0142658; 2017/0182248; 2017/0250971; 2018/0021514; 2018/0071454 and 2018/0193555 commonly owned U.S. patent application Ser. No. 14/707,851; and commonly owned U.S. Provisional Application Ser. Nos. 61/911,576; 61/920,902; 61/920,914; 61/920,940; 62/139,275; 62/352,164; 62/545,228; 62/655,516; 62/677,433; 62/743,901; 62/784,939; and 62/784,949.

Further incorporated by reference herein in their entirety are U.S. Pat. Nos. 8,601,465; 8,502,662; 8,452,953; 8,451,230; 8,449,523; 8,444,595; 8,343,092; 8,285,328; 8,126,728; 8,117,481; 8,095,123; 7,999,674; 7,819,843; 7,782,192; 7,109,878; 6,997,920; 6,979,326; 6,936,029; 6,872,200; 6,813,519; 6,641,533; 6,554,798; 6,551,276; 6,295,506; and 5,665,065.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. An ambulatory infusion pump system, comprising:
    a reservoir configured to contain a medicament, including a plunger at a proximal end of the reservoir and an outlet port at a distal end of the reservoir;
    a pushrod;
    a motor mechanically linked to the pushrod and configured to mechanically cause linear motion of the pushrod to contact and move the plunger to cause medicament to flow from the reservoir out of the outlet port to a patient;
    an optical encoder configured to monitor a linear position of the pushrod; and
    a processor configured to control the motor and pushrod to cause delivery of medicament from the reservoir, wherein the processor is configured to:
        command the motor to actuate to deliver medicament from the reservoir by advancing the pushrod from a first linear position to a second linear position;
        measure an amount of time for the pushrod to advance from the first linear position to the second linear position;
        compare the measured amount of time to an expected move completion time; and
        provide a notification of an error if the measured amount of time is longer than the expected move completion time, wherein the processor is further configured to determine if the pushrod moved from the first linear position to the second linear position, and if the pushrod moved from the first linear position to the second linear position, the notification indicates that the error is that an occlusion is present.

2. The ambulatory infusion pump system of claim 1, wherein the processor is further configured to determine an absolute position of the pushrod relative to a full retracted position and a full extended position if the pushrod did not move from the first linear position to the second linear position during the expected move completion time.

3. The ambulatory infusion pump system of claim 2, wherein the processor is configured to provide a notification of an error by notifying the user that the pushrod has reached the fully extended position if the pushrod is in the fully extended position.

4. The ambulatory infusion pump system of claim 2, wherein the processor is configured to determine an amount of medicament remaining in the reservoir if the pushrod is not in the fully extended position.

5. The ambulatory infusion pump system of claim 4, wherein the processor is configured to provide a notification that the reservoir needs to be refilled if the amount of medicament remaining in the reservoir is below a predetermined threshold.

6. The ambulatory infusion pump system of claim 4, wherein the processor is configured to provide a notification that a drive system error preventing the pushrod from being linearly advanced is present if the amount of medicament remaining in the reservoir is not below a predetermined threshold.

7. The ambulatory infusion pump system of claim 1, wherein the expected move completion time is an expected range of move completion times.

8. The ambulatory infusion pump system of claim 1, wherein the optical encoder monitors a linear position of the pushrod by monitoring a rotational position of markings on a drive tube that rotates when the motor is actuated to cause the linear motion of the pushrod.

9. An ambulatory infusion pump system, comprising:
a reservoir configured to contain a medicament, including a plunger at a proximal end of the reservoir and an outlet port at a distal end of the reservoir;
a pushrod;
a drive tube including a plurality of markings, the drive tube configured to cause linear motion of the pushrod when the drive tube is rotated, and wherein the markings comprise a predefined series of lines at least partially around the drive tube;
a motor configured to cause the drive tube to rotate to cause linear motion of the pushrod to contact and move the plunger to cause medicament to flow from the reservoir out of the outlet port to a patient;
an optical encoder configured to monitor a linear position of the pushrod by sensing the markings on the drive tube when the drive tube is rotated;
a magnetic sensor configured to monitor rotation of the drive tube by sensing a magnet disposed on the drive tube when the drive tube is rotated; and
a processor configured to compare rotation of the drive tube as monitored by the magnetic sensor sensing the magnet with rotation of the drive tube as monitored by the optical encoder sensing the markings on the drive tube, wherein the processor is configured to compare rotation of the drive tube by comparing a number of complete rotations of the drive tube as monitored by the magnetic sensor and the optical encoder.

10. The ambulatory infusion pump system of claim 9, wherein the processor is configured to compare rotation of the drive tube by comparing a number of markings sensed on the drive tube by the optical encoder with an expected number of markings expected to be detected for a given number of times the magnetic sensor has sensed the magnet.

11. The ambulatory infusion pump system of claim 10, wherein the expected number of markings is a range of markings.

12. The ambulatory infusion pump system of claim 9, wherein the processor is further configured to issue an encoder alert if the rotation of the drive tube as monitored by the magnetic sensor does not equal the rotation of the drive tube as monitored by the optical encoder.

13. The ambulatory infusion pump system of claim 9, wherein the processor is further configured to disable the motor if the rotation of the drive tube as monitored by the magnetic sensor does not equal the rotation of the drive tube as monitored by the optical encoder.

14. The ambulatory infusion pump system of claim 9, wherein the processor is further configured to initiate a pump self-test if the rotation of the drive tube as monitored by the magnetic sensor does not equal the rotation of the drive tube as monitored by the optical encoder.

15. The ambulatory infusion pump system of claim 9, wherein the magnetic sensor monitors rotation of the drive tube by sensing more than one magnet disposed on the drive tube.

16. An ambulatory infusion pump system, comprising:
a reservoir configured to contain a medicament, including a plunger at a proximal end of the reservoir and an outlet port at a distal end of the reservoir;
a pushrod;
a drive tube including a plurality of markings, the drive tube configured to cause linear motion of the pushrod when the drive tube is rotated, and wherein the markings comprise a predefined series of lines at least partially around the drive tube;
a motor configured to cause the drive tube to rotate to cause linear motion of the pushrod to contact and move the plunger to cause medicament to flow from the reservoir out of the outlet port to a patient;
an optical encoder configured to monitor a linear position of the pushrod by sensing the markings on the drive tube when the drive tube is rotated;
a magnetic sensor configured to monitor rotation of the drive tube by sensing a magnet disposed on the drive tube when the drive tube is rotated; and
a processor configured to compare rotation of the drive tube as monitored by the magnetic sensor sensing the magnet with rotation of the drive tube as monitored by the optical encoder sensing the markings on the drive tube, wherein the processor is further configured to initiate a pump self-test if the rotation of the drive tube as monitored by the magnetic sensor does not equal the rotation of the drive tube as monitored by the optical encoder.

17. The ambulatory infusion pump system of claim 16, wherein the processor is configured to compare rotation of the drive tube by comparing a number of complete rotations of the drive tube as monitored by the magnetic sensor and the optical encoder.

18. The ambulatory infusion pump system of claim 16, wherein the processor is configured to compare rotation of the drive tube by comparing a number of markings sensed on the drive tube by the optical encoder with an expected number of markings expected to be detected for a given number of times the magnetic sensor has sensed the magnet.

19. The ambulatory infusion pump system of claim 18, wherein the expected number of markings is a range of markings.

20. The ambulatory infusion pump system of claim 16, wherein the magnetic sensor monitors rotation of the drive tube by sensing more than one magnet disposed on the drive tube.

* * * * *